United States Patent
Suorsa et al.

[11] Patent Number: 6,120,454
[45] Date of Patent: Sep. 19, 2000

[54] ANNULAR ARRAY ULTRASOUND CATHETER

[75] Inventors: Veijo T. Suorsa, Sunnyvale; Niyazi Beyhan, Santa Clara, both of Calif.

[73] Assignee: Boston Scientific Corporation, Maple Grove, Minn.

[21] Appl. No.: 09/017,581

[22] Filed: Feb. 3, 1998

[51] Int. Cl.[7] ........................................ A61B 8/00
[52] U.S. Cl. ............................................. 600/466
[58] Field of Search .................. 600/459, 454, 600/450, 466, 467, 470, 468

[56] References Cited

U.S. PATENT DOCUMENTS

| | | | |
|---|---|---|---|
| 3,938,502 | 2/1976 | Bom | 128/2 |
| 4,155,259 | 5/1979 | Engeler | 73/626 |
| 4,576,177 | 3/1986 | Webster, Jr. | 128/660 |
| 4,771,774 | 9/1988 | Simpson et al. | 128/305 |
| 4,794,931 | 1/1989 | Yock | 128/660.03 |
| 5,095,911 | 3/1992 | Pomeranz | 128/662.06 |
| 5,108,411 | 4/1992 | McKenzie | 606/159 |
| 5,156,154 | 10/1992 | Valenta, Jr. et al. | 128/661.09 |
| 5,174,295 | 12/1992 | Christian et al. | 600/459 |
| 5,188,106 | 2/1993 | Naoppholz et al. | 128/419 |
| 5,203,338 | 4/1993 | Jang | 128/662.06 |
| 5,217,456 | 6/1993 | Narciso, Jr. | 606/15 |
| 5,273,045 | 12/1993 | Chihara et al. | 128/662.06 |
| 5,347,256 | 9/1994 | Yumiki et al. | 336/84 |
| 5,348,017 | 9/1994 | Thornton et al. | 128/622.06 |
| 5,359,312 | 10/1994 | Choi | 336/84 |
| 5,429,136 | 7/1995 | Milo et al. | 128/660.03 |
| 5,437,282 | 8/1995 | Koger et al. | 128/662.06 |
| 5,503,155 | 4/1996 | Salmon et al. | 128/662.06 |
| 5,549,108 | 8/1996 | Edwards et al. | 128/642 |
| 5,558,092 | 9/1996 | Unger et al. | 128/660.03 |
| 5,590,653 | 1/1997 | Aida et al. | 128/653.2 |
| 5,598,845 | 2/1997 | Chandraratna et al. | 128/662.03 |
| 5,620,417 | 4/1997 | Jang et al. | 604/96 |

FOREIGN PATENT DOCUMENTS

| | | |
|---|---|---|
| 0696435A2 | 6/1995 | European Pat. Off. |
| 19539163A | 10/1995 | Germany |
| WO89/04142 | 11/1988 | WIPO |
| WO98/39672 | 3/1998 | WIPO |

OTHER PUBLICATIONS

Roy W. Martin et al., "Design Characteristics for intravascular ultrasonic catheters," *International Journal of Cardiac Imaging 4*, pp. 201–216, 1989.

M. Arditi et al., "An Annular Array System for High Resolution Breast Echography," *Ultrasonic Imaging 4*, pp. 1–31, 1982.

R.B. Bernardi et al., "A Dynamically Focused Annular Array," 1976 Ultrasonics Symposium Proceedings, IEEE Cat. #76 CH1120–5SU, pp. 157–159.

*Primary Examiner*—Jeffrey R. Jastrzab

[57] ABSTRACT

The present invention provides for catheter systems and methods of their use. In one embodiment, the invention provides a catheter system comprising a catheter body having a distal end, a proximal end and a working lumen. A cable is disposed within the working lumen. A plurality of transducer elements, configured in an annular array, are operably attached to a distal end of the cable.

52 Claims, 5 Drawing Sheets

ANNULAR ARRAY ULTRASOUND CATHETER

BACKGROUND OF THE INVENTION

The present invention relates generally to the field of medical catheters, and in particular, to ultrasonic imaging medical catheters.

In recent years, the use of ultrasound systems for medical diagnostics has continued to grow. Ultrasonic systems are used in a plethora of medical fields and in a wide-ranging number of diagnostic areas. As the desire to use ultrasonic imaging systems has grown, so has the level of sophistication of those systems.

To assist physicians and staff in performing diagnostic and therapeutic procedures, a number of ultrasonic imaging systems have been designed for use with catheters. In general, these systems comprise a single transducer element, frequently made of piezoelectric material, attached to the distal portion of an imaging catheter. The imaging catheter is inserted into the patient and the transducer is positioned within the patient to image a desired region of the patient's anatomy.

Such catheters typically operate by sending an electrical signal or excitation pulse to the transducer. The transducer converts the electrical energy into mechanical energy, which propagates into a patient's surrounding body tissues as an ultrasonic wave. The frequency of the emitted ultrasonic waves are a function of the resonant frequency of the transducer element and the frequency content of the excitation pulse. The ultrasonic waves are reflected back to the transducer as reflected signals or echoes, which the transducer converts into an electrical signal. This electrical signal is used to produce an image of the patient's anatomy.

By operating with a single transducer, however, the images produced are limited to a single two-dimensional plane. As a result, the transducer must be moved within the patient to produce images over a larger area. Additionally, since the single transducer element has only one resonant frequency, the focusing capability of single transducer imaging catheters is limited. The frequency of emitted sound waves, which is a function of the resonant frequency and bandwidth of the transducer element and the frequency content of the excitation pulse, can only be varied by varying the excitation pulse frequency. As a result, the ability of a single transducer element to be focused at different depths into the surrounding tissue is limited.

It would be desirable, therefore, to provide an imaging catheter system capable of providing high quality ultrasound images. It is further desirable to provide for focusing in more than one plane to provide improved lateral resolution. It is also desirable to provide the capability to produce and receive multiple ultrasonic signals. It is further desirable to provide such a system for use with an ultrasonic imaging catheter.

SUMMARY OF THE INVENTION

The present invention provides for catheter systems and methods of their use. In one embodiment, the invention provides a catheter system comprising a catheter body having a distal end, a proximal end and a working lumen. A cable is disposed within the working lumen. A plurality of transducer elements, configured in an annular array, are operably attached to a distal end of the cable.

In one particular aspect, the cable comprises a drive cable. Such a cable is used to rotate the transducer elements, thereby facilitating the production of images of the patient's tissues surrounding the transducer elements.

In another aspect, the catheter system further includes a transmission line, disposed within the working lumen, and operably connected to the transducer elements. In one aspect, the transmission line comprises a coaxial cable. Alternatively, the transmission line comprises a twisted pair cable. In this manner, electrical signals can be sent to, and received from, the transducer elements.

In still another aspect, the catheter system further includes a plurality of transmission lines disposed within the working lumen. Each transducer element is operably connected to one transmission line. In one aspect, the annular array comprises at least two generally concentric transducer elements.

In a further aspect, the annular array defines a face which is circular in shape. In one aspect, the face is flat. Alternatively, the face may have a spherical, or other curvature. An annular array with a spherical curvature results in the focal point being closer to the face than if the face were flat. Such a configuration facilitates the production of clear images of a patient's anatomy located close to the transducer face. Alternatively, the annular array may define a face which is elliptical or oval in shape. The elliptical face may be flat, or have a spherical or elliptical curvature.

In one particular aspect, the catheter system further comprises at least one filter in communication with the transmission line to filter a communications signal transmitted through the transmission line. The filter is designed to allow a predetermined frequency range of the communications signal to pass through the filter. In this manner, the filter can filter out unwanted frequency ranges, allowing only a desired frequency range to pass to image processing equipment. In one aspect, the filter comprises a high pass filter and, in another aspect, the filter comprises a low pass filter. In a further aspect, the filter comprises a band pass filter.

In still another aspect, the catheter system further comprises a plurality of filters in communication with the transmission line to filter a plurality of communication signals transmitted through the transmission line. Each filter allows a different frequency range of the communication signals to pass through the filter. In this way, a single transmission line may be used with a plurality of transducer elements.

The invention further provides a catheter system comprising a catheter body having a distal end, a proximal end and a working lumen. A cable is disposed within the working lumen, and a plurality of transducer elements, configured in an annular array, are operably attached to a distal end of the cable. At least one transmission line is operably attached to the transducer elements and is disposed within the working lumen. The catheter body has an outer diameter that is smaller than about 20 French, to facilitate introduction into a body lumen.

In one aspect, the catheter system further comprises at least two concentric transducer elements. In another particular aspect, the catheter system further includes a plurality of transmission lines disposed within the working lumen. Each transducer element is operably connected to a single transmission line. In another aspect, the catheter body has an outer diameter that is between about 1 French and about 20 French.

In one particular aspect, the system further comprises at least one filter in communication with the transmission line to filter a communications signal transmitted through the transmission line. The filter allows a predetermined frequency range of the communications signal to pass through the filter. In one aspect, the filter is a high pass filter. Alternatively, the filter is a low pass filter or a band pass filter.

In one aspect of the invention, the catheter system further comprises a plurality of filters in communication with the transmission line to filter a plurality of communications signals transmitted through the transmission line. Each filter allows a different frequency range of the communication signals to pass through the filter. In this manner, a single transmission line is used for a plurality of transducer elements, thereby facilitating the use of catheter bodies with small outer diameters.

The present invention further provides an exemplary method for imaging a body lumen. The method includes the step of providing a catheter comprising a catheter body having a proximal end, a distal end and a working lumen. The catheter further includes a cable disposed within the working lumen and a plurality of transducer elements that are arranged in an annular array and are operably attached to the cable. The method further includes the step of coupling the catheter to a controller. The catheter is introduced into a patient and the transducer elements are positioned within a body lumen. The method further includes energizing the transducer elements and rotating the transducer elements while capturing at least one reflected signal. The reflected signal is transmitted to the controller, and at least one image of the body lumen is produced based on the reflected signal.

In one aspect of the method, the transmitting step comprises transmitting the reflected signal through a transmission line disposed within the working lumen. In this aspect, the transmission line is operably connected to the transducer elements in order to transmit a reflected signal from the transducers.

In another aspect of the method, the transmitting step comprises transmitting a plurality of reflected signals through a plurality of transmission lines disposed within the working lumen. Each transducer element is operably connected to one transmission line. In an alternative aspect, a plurality of reflected signals are transmitted through a single transmission line disposed within the working lumen, with the transmission line being operably connected to the transducer elements.

In one aspect, the annular array comprises at least two transducer elements, and the capturing step comprises capturing at least two reflected signals. In another aspect, the method further comprises the step of filtering the reflected signal to facilitate signal processing before producing an image of the body lumen. In one aspect, the reflected signal is filtered with a low pass filter. Alternatively, the reflected signal is filtered with a high pass filter or a band pass filter. In still another aspect of the method, a plurality of reflected signals are filtered with a plurality of filters.

In a further aspect of the method, the energizing step comprises energizing less than all of the transducer elements so that the aperture of the annular array is reduced. Such a method is beneficial for imaging close to the annular array. In one aspect, only the centermost transducer element is energized. In another aspect, only the two centermost transducer elements are energized.

In another aspect of the method, the image of the body lumen is produced using a zone focusing technique. In still another aspect, the image of the body lumen is produced using a dynamic focusing technique. In a further aspect, a plurality of reflected signals are used to produce a single image of a body lumen.

DESCRIPTION OF THE PREFERRED EMBODIMENT

Figure 1:
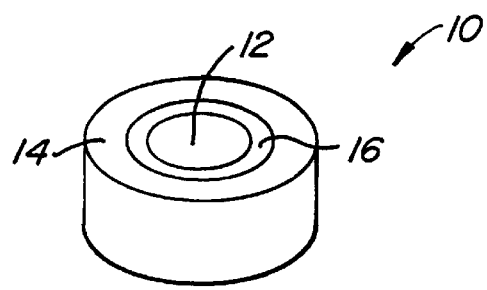
FIG. 1 is perspective view of an annular array of transducer elements according to the present invention.

The present invention provides for catheter systems and methods of their use. Specifically, the present invention provides an annular array of transducer elements for use in an imaging catheter system.

Annular arrays according to the present invention contain a plurality of generally concentric transducer elements located around a central axis. Such arrays can be used with focusing techniques commonly known as "dynamic focusing" or "zone focusing".

Dynamic focusing may be used when the transducer elements are simultaneously excited by an electrical energy pulse. The transducer elements (which may be constructed from piezoelectric ceramic materials, piezocomposite materials, piezoelectric plastics, and the like) convert the electrical energy pulse into mechanical energy, which propagates out from the face of the transducer in the form of an ultrasonic wave. The frequency of this ultrasonic wave is dependent upon the excitation frequency and the transducer element's natural resonant frequency and its bandwidth.

When the ultrasonic waves impinge on an object, such as a change in material within a body lumen, the ultrasonic waves are reflected back to the transducers, which then convert the mechanical energy back into an electrical signal. The electrical signal from each transducer is transmitted from the distal end of the catheter to the catheter system's imaging equipment by a transmission line.

However, because of the configuration of the annular array, the reflected signal is received at different times by the individual transducer elements. In other words, when the ultrasonic wave impinges on an object along the central axis of the annular array, the reflected wave is received by the central element before the reflected wave is received by an element along the outer ring of the annular array.

The present invention may use a compensation circuit contained in a controller to adjust the reflected signals to take into account the time delays resulting from the different distances the waves travel. Commonly referred to as "dynamic focusing", this method of compensation allows for improved resolution, particularly close to the transducer face.

Alternatively, the present invention may use an imaging method commonly known as "zone focusing." Zone focusing occurs when transmitted signals to the center array elements are delayed relative to the outer elements. As a result, a wavefront of ultrasonic energy propagates into the surrounding tissue and converges into a first focal zone within the tissue due to the time delay of transmissions between the inner and outer transducer elements. The reflected signals which propagate back from this zone to the transducer elements are processed by using the same time delay sequences and are summed, thereby producing a focused image from the first zone.

The transmission time delays are then adjusted to produce a wavefront from the array elements that converges into a second focal zone within the tissue, at a greater distance from the array than the first focal zone. Similarly, the reflected signals are processed in a manner which focuses the receiver within the second focal zone. This approach continues for as many zones as needed to produce an image of sufficient depth into the surrounding tissue. As a result, the zone focusing technique, although slower than dynamic focusing, produces better lateral resolution and good sensitivity.

Dynamic and zone focusing techniques are further described in U.S. Pat. No. 4,155,259; "A Dynamically Focused Annular Array" by R. B. Bernardi et. al., 1976 *Ultrasonics Symposium Proceedings,* IEEE Cat. #76 CH 1120-5SU; and "An Annular Array System For High Resolution Breast Echography" by M. Arditi et. al., *Ultrasonic Imaging* 4, p. 1–31 (1982), the disclosures of which are hereby incorporated by reference.

By using a catheter comprising an annular array of transducer elements according to the present invention, with either dynamic focusing or zone focusing, the catheter is capable of producing high quality ultrasound images with improved lateral resolution compared to single transducer catheters. In particular, the annular array of transducer elements of the invention are capable of producing multiple ultrasonic signals and then focusing the ultrasonic waves at different depths into the surrounding tissues. The transmission of multiple ultrasonic signals to image processing equipment can be accomplished, for example, by using the rotary transformer disclosed in copending U.S. patent application Ser. No. 09/017,583 (attorney reference number 12553-006500), filed contemporaneously herewith, the disclosure of which is hereby incorporated by reference.

Turning now to FIG. 1, an annular array 10 according to the present invention will be described. Annular array 10 comprises two transducer elements, a central transducer element 12 surrounded by a second transducer element 14. Transducer elements 12, 14 are generally concentric and are preferably made of piezocomposite materials; however, they may also comprise piezoceramic materials (such as PZT), piezoplastics, and the like. For an annular array using transducer elements comprising piezoelectric or piezoceramic materials, a spacer or kerf 16 is required between the elements. Kerf 16 comprises a nonconductive material, such as air or epoxy and the like, in order to lessen the chance that electrical or acoustic signals will be transferred between transducer elements 12, 14. Other transducer element materials, such as composites, will not require kerf 16 and, as a result, transducer element 12 and transducer element 14 can be placed adjacent one another.

Figure 2A:
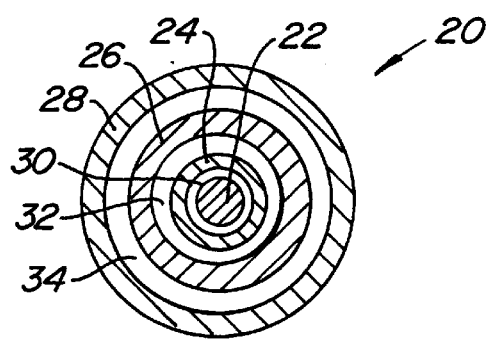
FIGS. 2A and 2B are cross sectional front views of alternative embodiments of an annular array of transducer elements according to the present invention.
Figure 2B:
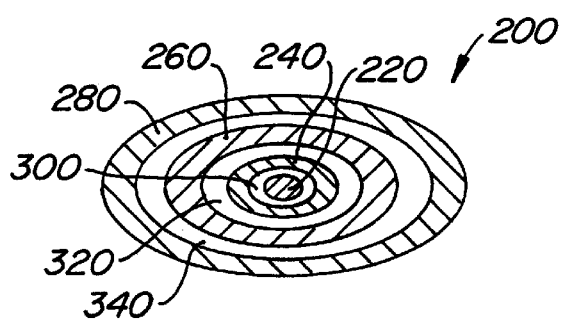

FIG. 2A depicts a cross section of a four element annular array 20. Similar to the embodiment of FIG. 1, annular array 20 comprises a series of generally concentric transducer elements 22, 24, 26, 28. Depending on the transducer material used, a number of kerfs 30, 32, 34 may be required between the transducer elements (cross-hatching not shown for convenience of illustration). FIG. 2B depicts a cross section of an alternative embodiment of an annular array according to the present invention. Annular array 200 comprises a series of generally concentric transducer elements 220, 240, 260, 280. Depending on the transducer material used, a number of kerfs 300, 320, 340 may be required between the transducer elements (cross-hatching not show for convenience of illustration). While FIGS. 2A and 2B depict annular arrays comprising four transducer elements, it will be appreciated that the number of transducer elements may be larger or smaller than four. An annular array according to the present invention will preferably use between about two (2) and about fifteen (15) transducer elements, and more preferably, between about two (2) and about seven (7) transducer elements.

Figure 3A:
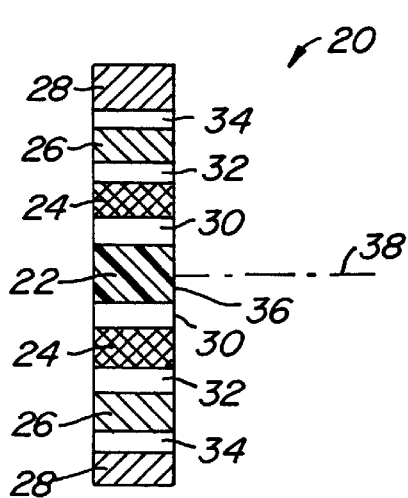
FIG. 3A is a cross-sectional side view of the annular array of transducer elements depicted in FIG. 2A.

FIG. 3A depicts a cross-sectional side view of the annular array 20 described in conjunction with FIG. 2A. Specifically, FIG. 3A depicts annular array 20 having a face 36 that is flat. As a result of this flat-faced configuration, electric signals received by transducer elements 22, 24, 26, 28 are converted into mechanical energy which propagates out from each transducer element 22, 24, 26, 28 as an ultrasonic wave. Ultrasonic waves from each of the four elements converge at a focal point along a central axis 38 of the annular array.

Figure 3B:
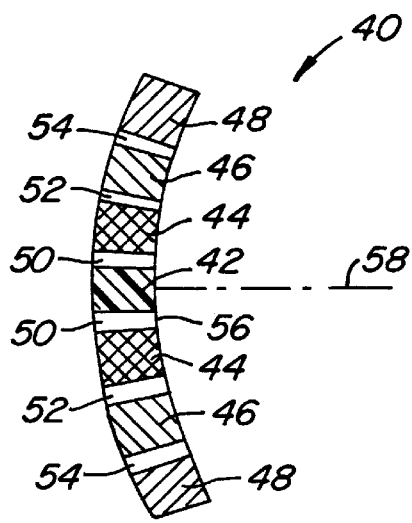
FIG. 3B is a cross-sectional side view of an alternative embodiment of an annular array of transducer elements according to the present invention.

FIG. 3B depicts an alternative embodiment of an annular array of transducer elements 40. Annular array 40 comprises transducer elements 42, 44, 46, 48. As in FIG. 3A, this embodiment may also require, depending on the transducer materials used, a number of kerfs 50, 52, 54 located between transducer elements 42, 44, 46, 48. The annular array of transducer elements 40 has a face 56 with a spherical curvature. Such a configuration moves the focal point of the annular array 40 closer to the face 56 along central axis 58. Other curvatures of face 56, such as an elliptical curvature, may also be used. As best seen in FIGS. 2A and 2B, the annular array face may be circular in shape (FIG. 2A) or elliptical or oval in shape (FIG. 2B).

Figure 4:
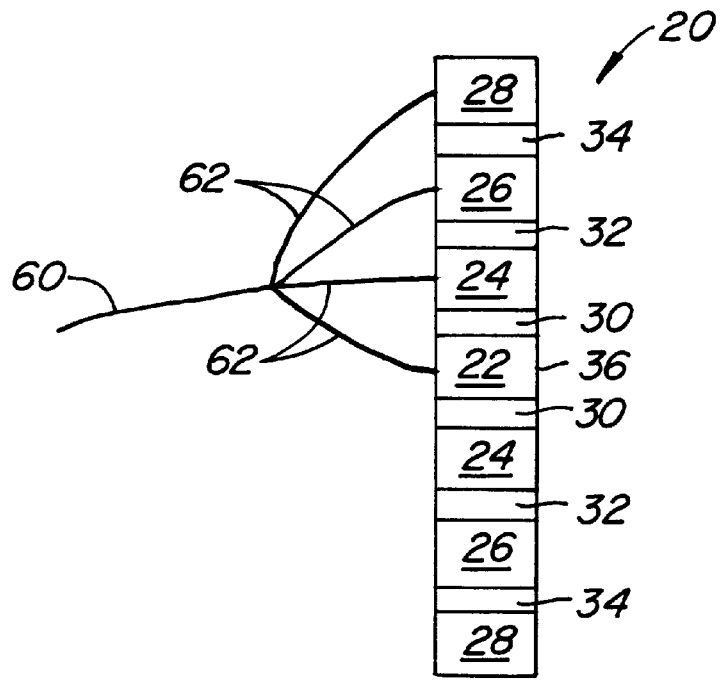
FIG. 4 is a schematic view of the annular array of transducer elements depicted in FIG. 2, operably connected to a single transmission line.

Turning now to FIG. 4, annular array 20 coupled to a single transmission line 60 will be described. As previously noted, annular array 20 comprises transducer elements 22, 24, 26, 28 concentrically configured around a central axis running through the approximate center of the annular array, i.e., through the approximate center of transducer element 22. Transmission line 60 is used to connect the transducer elements 22, 24, 26, 28 to image processing equipment. A number of leads 62 connect the transducer elements 22, 24, 26, 28 to the transmission line 60. In this manner, a single transmission line, running the length of the catheter body and connected to image processing equipment, can be used to carry electric signals to and from all transducer elements 22, 24, 26, 28 of annular array 20.

Figure 5:
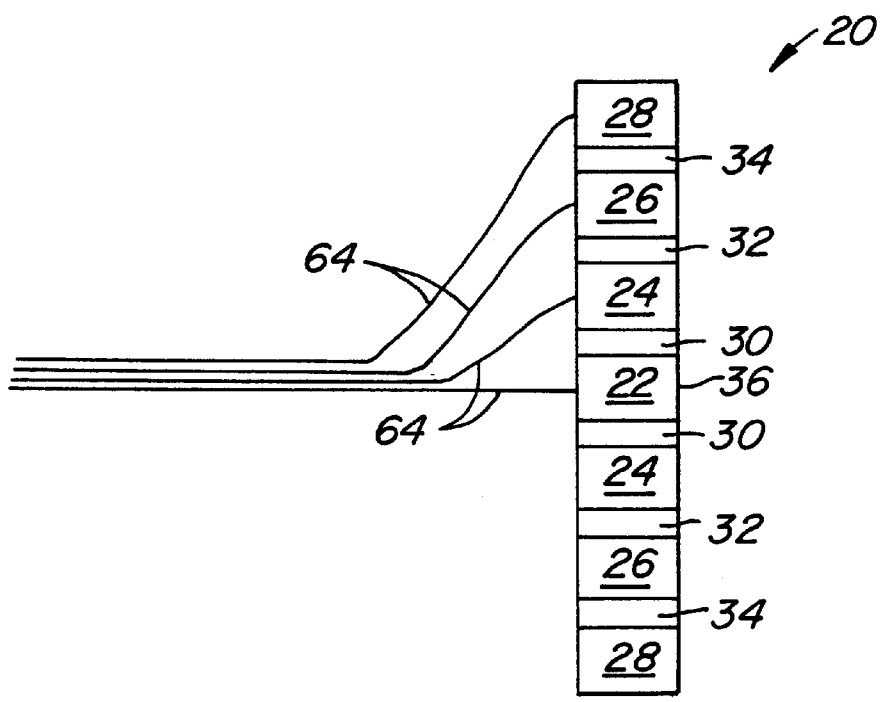
FIG. 5 is a schematic view of the annular array of transducer elements depicted in FIG. 2, operably connected to a plurality of transmission lines.

In an alternative embodiment depicted in FIG. 5, transducer elements 22, 24, 26, 28 are each connected to a separate transmission line 64. In this configuration, transmission lines 64 are connected to image processing equipment located outside the catheter body in order to receive and process electrical signals coming from the transducer elements 22, 24, 26, 28. Depending on the number and type of transmission lines 64 used, this configuration may require a catheter body having a larger outer diameter in order to accommodate a plurality of transmission lines 64.

Figure 6:
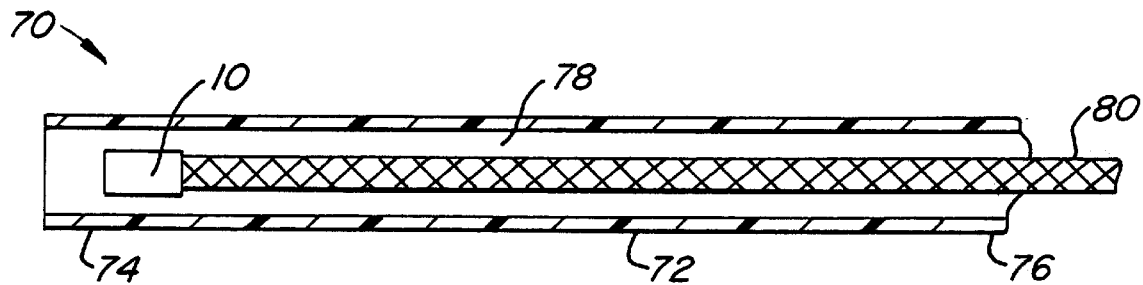
FIG. 6 is a cross sectional view of a catheter system having an annular array of transducer elements according to the present invention.

FIG. 6 depicts a catheter system 70, which incorporates annular array 10 and comprises a catheter body 72 having a distal end 74 and a proximal end 76. The catheter system 70 further includes a working lumen 78 in which a cable 80 is received. Annular array 10 is operably attached to a distal end of cable 80. In this manner, rotation of cable 80, and hence rotation of the annular array 10, can occur with respect to a generally stationary catheter body 72. The annular array 10 may alternatively be configured with a variety of shapes. As previously described, the annular array may comprise a plurality of generally circular, concentric transducer elements. Alternatively, a plurality of generally elliptical, concentric transducer elements may be used.

Exemplary catheter bodies which may be used with the annular array of transducer elements 10 include those disclosed in U.S. Pat. No. 4,794,931, U.S. Pat. No. 5,203,338, and U.S. Pat. No. 5,620,417, the disclosures of which are hereby incorporated by reference. Cables and transmission lines which may be used with the present invention include those disclosed in copending U.S. patent application Ser. No. 09/017,578 (attorney reference 12553-006400), filed contemporaneously herewith, and in U.S. Pat. No. 5,503,155 and U.S. Pat. No. 5,108,411, the disclosures of which are hereby incorporated by reference.

Figure 7B:
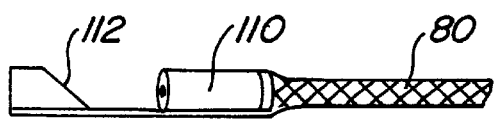
FIG. 7A and 7B depict two alternative embodiments of the annular array of the catheter system depicted in FIG. 6.
Figure 7A:
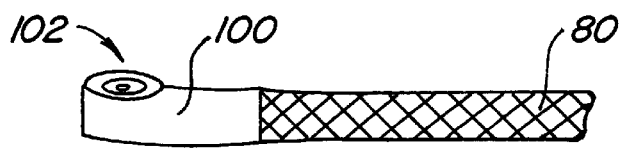

FIGS. 7A and 7B depict two alternative arrangements of an annular array operably attached to the distal end of cable 80. FIG. 7A depicts an annular array of transducer elements 100 capable of transmitting ultrasonic waves into a patient's surrounding tissue as cable 80 is rotated. The annular array face 102 faces out into the surrounding tissue of the patient's anatomy. FIG. 7B likewise is configured to emit ultrasonic waves into the surrounding tissue. However, FIG. 7B has an annular array of transducer elements 110 that is axially aligned with cable 80. Such a configuration requires the reflection of ultrasonic sound waves by a mirror 112 angled at approximately 45 degrees, in order to project ultrasonic sound waves into the surrounding tissue. Likewise, reflected signals from the tissue reflect off of mirror 112 and are received by the annular array of transducer elements 110.

Figure 8:
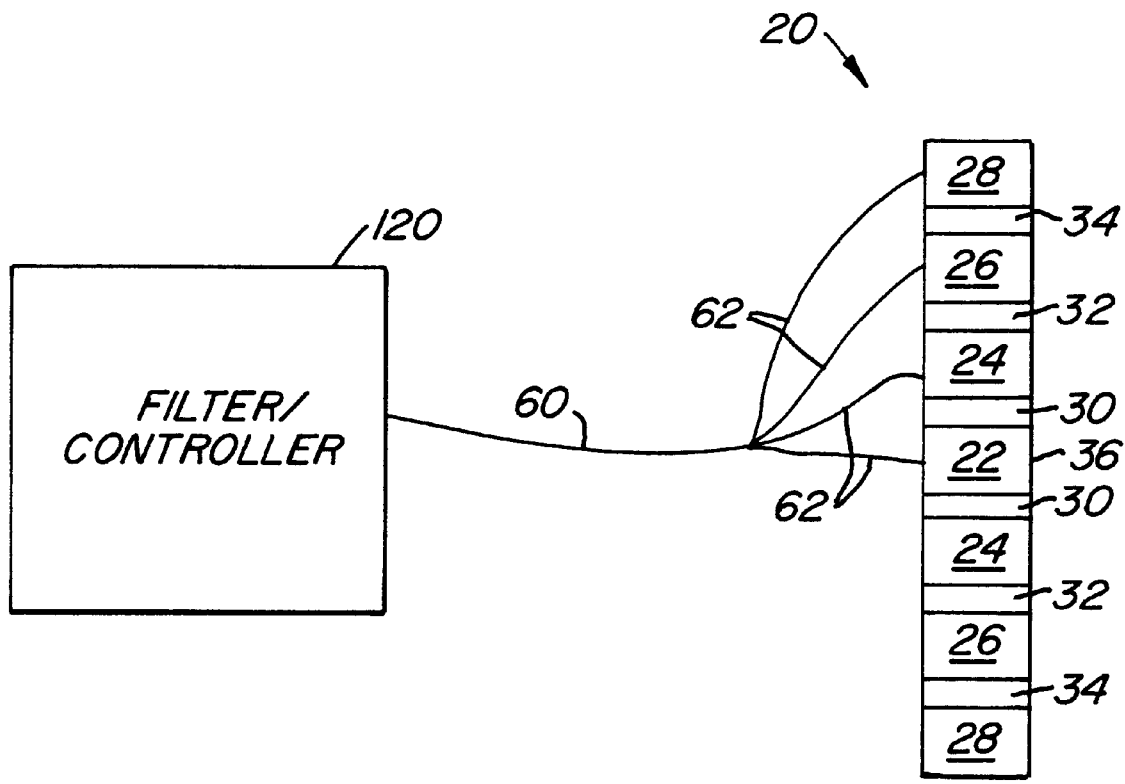
FIG. 8 is a schematic view of the annular array of transducer elements depicted in FIG. 4, operably connected to a filter/controller.

FIG. 8 depicts the annular array 20 as previously discussed in conjunction with FIG. 4, connected to a filter/controller 120. Because this embodiment uses a single transmission line 60 to transmit electrical signals to and from a plurality of transducer elements 22, 24, 26, 28, a system for controlling and processing the electrical signals is provided. The filter/controller 120 is used to control signals sent to and received from the transducer elements 22, 24, 26, 28 as described in greater detail hereinafter.

Figure 9:
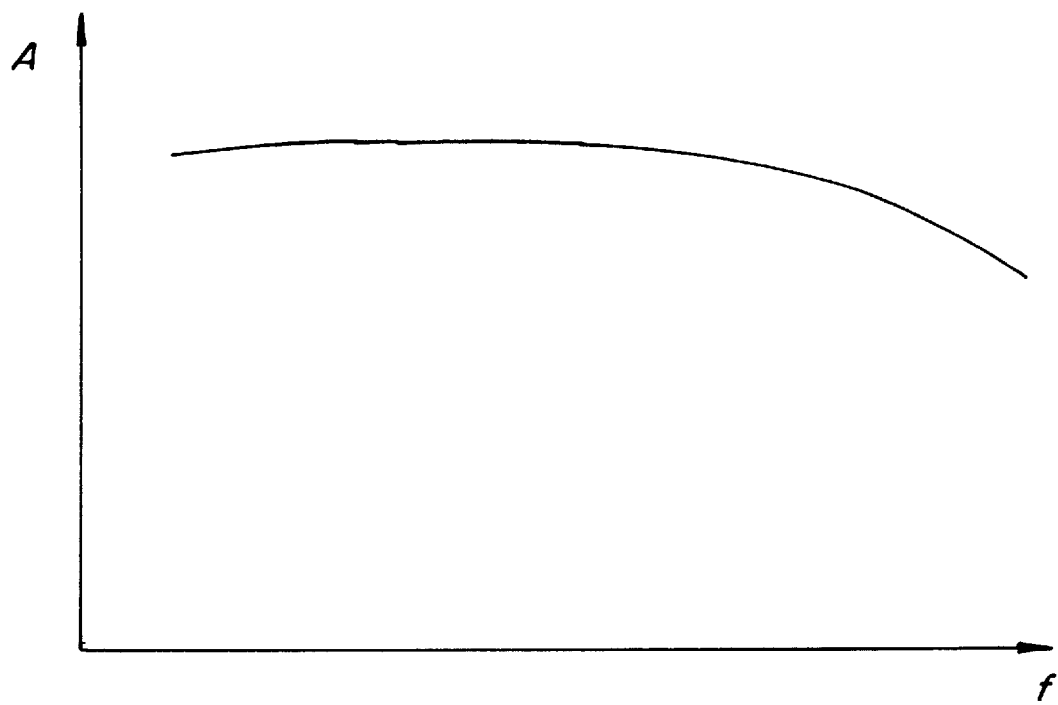
FIG. 9 is a representative frequency and amplitude plot of an excitation pulse as used according to the method of the present invention.

A method of using a single transmission line 60 for transmitting multiple transducer element signals will now be described. The frequency at which the transducer elements 22, 24, 26, 28 emit ultrasonic waves is a function of a resonant frequency of each transducer element 22, 24, 26, 28 and the frequency of the excitation pulse sent to the transducer elements 22, 24, 26, 28. By configuring different transducer elements 22, 24, 26, 28 in the annular array 20 to resonate at different frequencies, and then using a broad banded excitation pulse emitted over the full frequency range of all transducer elements 22, 24, 26, 28 in the array, the return signals received from those transducer elements will vary in frequency. FIG. 9 depicts a frequency and amplitude plot of an excitation pulse used to excite transducer elements 22, 24, 26, 28. The broadbanded nature of such a pulse results in the excitation of each transducer element 22, 24, 26, 28.

By configuring transducer elements 22, 24, 26, 28 to each operate at a different resonant frequency, electrical signals returning from the transducers 22, 24, 26, 28 comprise distinct frequency characteristics depending on the particular transducer element the signal is returning from. As a result, a single transmission line 60 can be used to carry a plurality of signals from transducer elements 22, 24, 26, 28 to the filter/controller 120. The filter/controller 120 uses a plurality of frequency filters, such as high pass, low pass and band pass filters, to filter out undesired frequency ranges and separate the signals.

Figure 10:
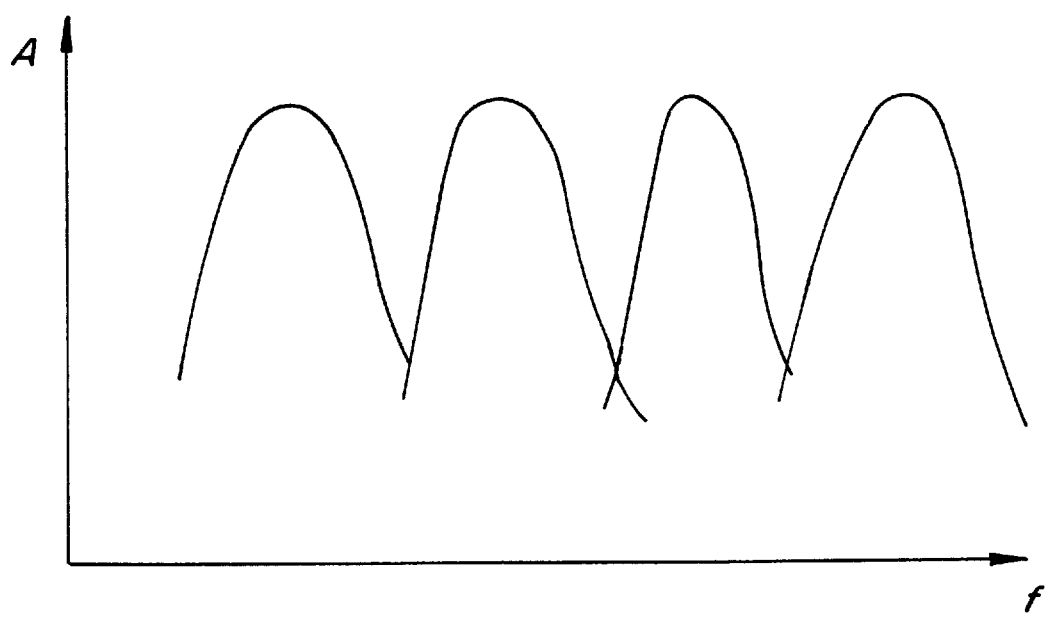
FIG. 10 is a representative frequency and amplitude plot of a plurality of reflected signals as received according to the method of the present invention.

For example, a single transmission line can transmit four signals to the filter/controller 120 which sends the signals to four different filters. Each filter can be "tuned" to the frequency of a particular transducer element, such that each filter allows only a portion of the frequency range corresponding to one transducer element to pass through. By using frequency filters in the desired frequency ranges, the filter/controller 120 can separate out the returning signals. FIG. 10 depicts four filtered signals received from four different transducers 22, 24, 26, 28. The filter/controller 120 then uses one or more signals to produce an image of a body lumen.

For imaging close to the face 36 of annular array 20, it may be desirable to use only transducer elements near the center of annular array 20. By exciting only the centermost transducer elements, an aperture of the annular array 20 is reduced. For example, in annular array 20 depicted in FIG. 5, only transducer element 22 would be excited. In this manner, only the centermost transducer element 22 is used to produce an image close to the array face 36. Similarly, transducer elements 22, 24 could be excited. In this manner, the two centermost transducer elements 22, 24 of annular array 20 would be used, thereby reducing the aperture of annular array 20.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A catheter system comprising;
    a catheter body having a distal end, a proximal end, a longitudinal axis and a working lumen;
    a cable disposed within the working lumen; and
    a plurality of transducer elements configured in an annular array around an array central axis, wherein the annular array is operably attached to a distal end of the cable so that said array central axis is positioned at a non-zero angle relative to said longitudinal axis.

2. A catheter system as in claim 1, wherein the cable comprises a drive cable that is adapted to rotate said annular array.

3. A catheter system as in claim 1, further comprising a transmission line disposed within the working lumen, wherein the transmission line is operably connected to the transducer elements.

4. A catheter system as in claim 3, wherein the transmission line comprises a coaxial cable.

5. A catheter system as in claim 3, wherein the transmission line comprises a twisted pair cable.

6. A catheter system as in claim 3, further comprising at least one filter in communication with the transmission line to filter a communications signal transmitted through the transmission line, wherein the filter allows a predetermined frequency range of said communications signal to pass through the filter.

7. A catheter system as in claim 6, wherein the filter comprises a high pass filter.

8. A catheter system as in claim 6, wherein the filter comprises a low pass filter.

9. A catheter system as in claim 6, wherein the filter comprises a band pass filter.

10. A catheter system as in claim 3, further comprising a plurality of filters in communication with the transmission line to filter a plurality of communication signals transmitted through the transmission line, wherein each filter allows a different frequency range of said communication signals to pass through the filter.

11. A catheter system as in claim 1, further comprising a plurality of transmission lines disposed within the working lumen, wherein each transducer element is operably connected to one transmission line.

12. A catheter system as in claim 1, wherein the annular array comprises at least two concentric transducer elements with one of said transducer elements defining a central element of said annular array through which said array central axis passes.

13. A catheter system as in claim 1, wherein the annular array defines a face which is generally circular in shape.

14. A catheter system as in claim 13, wherein the face is flat.

15. A catheter system as in claim 13, wherein the face has a spherical curvature.

16. A catheter system as in claim 1, wherein the annular array defines a face which is generally elliptical in shape.

17. A catheter system as in claim 16, wherein the face is flat.

18. A catheter system as in claim 16, wherein the face has a spherical curvature.

19. A catheter system as in claim 16, wherein the face has an elliptical curvature.

20. A catheter system as in claim 1, wherein said annular array is operably attached to said distal end so that said central axis is generally perpendicular to said longitudinal axis.

21. A catheter system comprising;
a catheter body having a distal end, a proximal end, a longitudinal axis and a working lumen;
a cable disposed within and adapted to rotate within the working lumen;
a plurality of transducer elements configured in an annular array, wherein the annular array is operably attached to a distal end of the cable so that said annular array is positioned to project an ultrasound signal into an image plane that is at a non-zero angle relative to said longitudinal axis;
at least one transmission line operably attached to the transducer elements, wherein the transmission line is disposed within the working lumen; and
wherein the catheter body has an outer diameter that is smaller than about 20 French, to facilitate introduction into a body lumen.

22. A catheter system as in claim 21, further comprising at least two concentric transducer elements.

23. A catheter system as in claim 21, wherein the annular array defines a face which is generally circular in shape.

24. A catheter system as in claim 23, wherein the face is flat.

25. A catheter system as in claim 23, wherein the face has a spherical curvature.

26. A catheter system as in claim 21, wherein the annular array defines a face which is generally elliptical in shape.

27. A catheter system as in claim 26, wherein the face is flat.

28. A catheter system as in claim 26, wherein the face has a spherical curvature.

29. A catheter system as in claim 26, wherein the face has an elliptical curvature.

30. A catheter system as in claim 21, further comprising a plurality of transmission lines disposed within the working lumen, wherein each transducer element is operably connected to one transmission line.

31. A catheter system as in claim 21, wherein the catheter body has an outer diameter that is between about 1 French and about 20 French.

32. A catheter system as in claim 21, further comprising at least one filter in communication with the transmission line to filter a communications signal transmitted through the transmission line, wherein the filter allows a predetermined frequency range of said communications signal to pass through the filter.

33. A catheter system as in claim 32, wherein the filter is selected from a group of filters consisting of a high pass filter, a low pass filter and a band pass filter.

34. A catheter system as in claim 21, further comprising a plurality of filters in communication with the transmission line to filter a plurality of communications signals transmitted through the transmission line, wherein each filter allows a different frequency range of said communication signals to pass through the filter.

35. A method for imaging a body lumen, the method comprising the steps of:
providing a catheter comprising a catheter body having a proximal end, a distal end, a longitudinal axis and a working lumen, wherein a cable is disposed within the working lumen and a plurality of transducer elements that are arranged in an annular array are operably attached to the cable;
coupling the catheter to a controller;
introducing the catheter into a patient and positioning the transducer elements within a body lumen;
energizing at least one of the transducer elements so that said at least one transducer element projects an ultrasound signal in a direction that is not coaxial with said longitudinal axis;
rotating the transducer elements while capturing at least one reflected signal;
transmitting the reflected signal to the controller; and
producing at least one image of the body lumen based on the reflected signal.

36. A method as in claim 35, wherein the transmitting step comprises transmitting the reflected signal through a transmission line disposed within the working lumen, wherein the transmission line is operably connected to the transducer elements.

37. A method as in claim 35, wherein the transmitting step comprises transmitting a plurality of reflected signals through a plurality of transmission lines disposed within the working lumen, wherein each transducer element is operably connected to one transmission line.

38. A method as in claim 35, wherein the transmitting step comprises transmitting a plurality of reflected signals through a single transmission line disposed within the working lumen, wherein the transmission line is operably connected to the transducer elements.

39. A method as in claim 35, wherein the annular array comprises at least two transducer elements, and wherein the capturing step comprises capturing at least two reflected signals.

40. A method as in claim 35, further comprising the step of filtering the reflected signal to facilitate signal processing before producing an image of the body lumen.

41. A method as in claim 40, wherein the filtering step comprises filtering the reflected signal with a low pass filter.

42. A method as in claim 40, wherein the filtering step comprises filtering the reflected signal with a high pass filter.

43. A method as in claim 40, wherein the filtering step comprises filtering the reflected signal with a band pass filter.

44. A method as in claim 40, wherein the filtering step comprises filtering a plurality of reflected signals with a plurality of filters.

45. A method as in claim 35, wherein the energizing step comprises energizing less than all of the transducer elements so that an aperture of the annular array is reduced.

46. A method as in claim 45, wherein the energizing step comprises energizing only a centermost of the transducer elements of the annular array.

47. A method as in claim 45, wherein the energizing step comprises energizing only the two centermost transducer elements of the annular array.

48. A method as in claim 45, wherein the image of the body lumen is produced using a zone focusing technique.

49. A method as in claim 45, wherein the image of the body lumen is produced using a dynamic focusing technique.

50. A method as in claim 35, wherein the transmitting step comprises transmitting a plurality of reflected signals and the producing step comprises producing a single image of said body lumen based on said plurality of reflected signals.

51. A method as in claim 35, wherein said energizing and rotating steps occur simultaneously so that said ultrasound signal is projected into an image plane that is at a non-zero angle relative to said longitudinal axis.

52. A method as in claim 51, wherein said image plane is a 360 degree image plane positioned generally perpendicular to said longitudinal axis.

* * * * *

UNITED STATES PATENT AND TRADEMARK OFFICE
CERTIFICATE OF CORRECTION

PATENT NO.     : 6,120,454
DATED          : September 19, 2000
INVENTOR(S)    : Veijo T. Suorsa and Niyazi Beyhan It is certified that two errors appear in the above-identified patent and that said Letters Patent is hereby corrected as shown below:

In claim 48, please delete "as in claim 45," and insert --as in claim 35,--

In claim 49, please delete "as in claim 45," and insert --as in claim 35,--

Signed and Sealed this

Seventeenth Day of April, 2001

Attest:

NICHOLAS P. GODICI

Attesting Officer

Acting Director of the United States Patent and Trademark Office